United States Patent [19]  [11] 3,943,244
Cook et al. [45] Mar. 9, 1976

[54] ANTI-MICROBIAL FACTORS EFFECTIVE AGAINST BACILLIC AND COCCIC INFECTIONS

[75] Inventors: Elton S. Cook, Cincinnati, Ohio; Norbert J. Berberich, Jr., Burlington, Ky.

[73] Assignee: Stanley Drug Products, Inc., Portland, Oreg.

[22] Filed: Oct. 26, 1972

[21] Appl. No.: 301,239

Related U.S. Application Data

[63] Continuation-in-part of Ser. No. 117,765, Feb. 22, 1971, abandoned.

[52] U.S. Cl. .............................................. 424/95
[51] Int. Cl.² .................. A61K 35/12; A61K 35/56
[58] Field of Search ....................................... 424/95

[56] References Cited

UNITED STATES PATENTS 1,437,951  12/1922  Archibald ............................ 424/95
2,171,320  8/1939  Lautenschlager et al. ............. 424/95

OTHER PUBLICATIONS

Notini et al., Nature, Vol. 156, 1945, pp. 419–420.
Notini et al., V. of Bacteriology, Vol. 52, 1946, pp. 681–684.

Primary Examiner—Jerome D. Goldberg
Assistant Examiner—D. W. Robinson
Attorney, Agent, or Firm—John G. Schenk

[57] ABSTRACT

Factors effective in reducing the incidence of deleterious effects of infections due to cocci and bacilli are derived by gel filtration from animal tissues.

3 Claims, 1 Drawing Figure

ANTI-MICROBIAL FACTORS EFFECTIVE AGAINST BACILLIC AND COCCIC INFECTIONS

BACKGROUND OF THE INVENTION

This is a continuation-in-part of application Ser. No. 117,765 filed Feb. 22, 1971, now abandoned.

This invention pertains to substances possessing antimicrobiological activity and to processes for obtaining these factors. Until fairly recently normal skin and mucosal surfaces were thought to pose impenetrable barriers to the passage of most microorganisms. However, it is now known that various tissues of the body are frquently exposed to an assortment of microorganisms. One must, therefore, explain the failure of bacteria to proliferate once they have penetrated the tissues. There is experimental evidence that in healthy mammals the tissues themselves contain agents or antimicrobial factors which inhibit proliferation, or even survival of microorganisms.

Human studies of normal tissues indicate that such tissues contain various substances exerting antimicrobiological action. In fact investigations along these lines have been conducted in our laboratories for over a quarter of a century. This work has centered around nonspecific materials present in animal tissues. Extracts of beef brain and spleen have been most consistently used although other organs and tissues were also employed in exploratory investigations.

Nutini and Lynch, reported in Nature, Vol. 156, 1945, page 419 and Journal of Bacteriology, Vol. 52, 1946, page 681 that crude extracts of beef brain when administered prophylactically in vivo gave very significant degrees of protection to mice against staphylococcal infections. The same extract was found to be effective therapeutically as well. When used in vitro, the extract was reported to convert the yellow S variety (virulent) to an avirulent, white R type.

Even though much work has been conducted with anti-staphylococcic factors in brain and spleen of mammals for over two decades, our knowledge in this area has remained inadequate. In fact the whole area of basic mechanisms of virulence, pathogenicity and the closely related aspects of host-parasite relationships in staphylococcal and similar infections such as streptococcus is largely understood and offers an immense variety of problems. Much of this today is speculative or teleological; and even though the ability of alcoholic precipitated extracts of beef brain in prophylactic and therapeutic treatment for staphylococcus infections is confirmed, various other materials present in crude extract along with the active principle render their wide use improbable.

Attempts have been made to fractionate the crude extracts and to isolate the active principle. Direct or indirect solvent extraction methods have been used, but results are inconsistent and duplication of work is very difficult. In addition since ether, chloroform, pyridine and phenol are frequently employed, solvent extraction has the disadvantage that various required solvents present later toxicity problems. In the past, fractions have been contaminated with toxic amounts of solvent. Solvent extraction has, therefore, been only partially successful. The methods are too systematic and demanding in detail for commercial application.

Much of the work on the isolation of the active principle from animal tissue extracts has involved the use of ion exchange resins. This, however, has met with only limited success. One of the disadvantages of ion exchange resins is that since their use is based primarily on differences in electric charges of substances to be separated, a high degree of resolution does not seem to be achievable in the case of tissue extracts. Active fractions have been derived, but further purification is indicated. Removal of materials present in the fractions has been difficult. Some materials present in the fractions are believed to have a deleterious effect on experimental animals, tending to mask the antimicrobial activity of the fraction. It can be seen, therefore, that because of the complexities of brain and spleen extracts, active fractions have not been isolated from them with a degree of precision sufficient to benefit the public.

SUMMARY OF THE INVENTION

Crude brain or spleen alcohol extracts, although reported as effective, are not completely suitable as active principles having antimicrobial activity. When they are used, large doses, of, say, greater than 500 miligrams, are necessary. Moreover variations between batches of brain extracts have been encountered. In addition because of their complex chemical nature results vary from host to host. Hence they are not sufficiently reliable for administration. In accordance with this invention an extremely concentrated, and hence less complex chemically, antimicrobial factor, factor Z herein, is derived from alcohol extract of mammalian brain or spleen by gel filtration of the crude extract. The factor is particularly effective against infections due to cocci and bacilli.

DETAILED DESCRIPTION OF THE INVENTION

Figure 1:
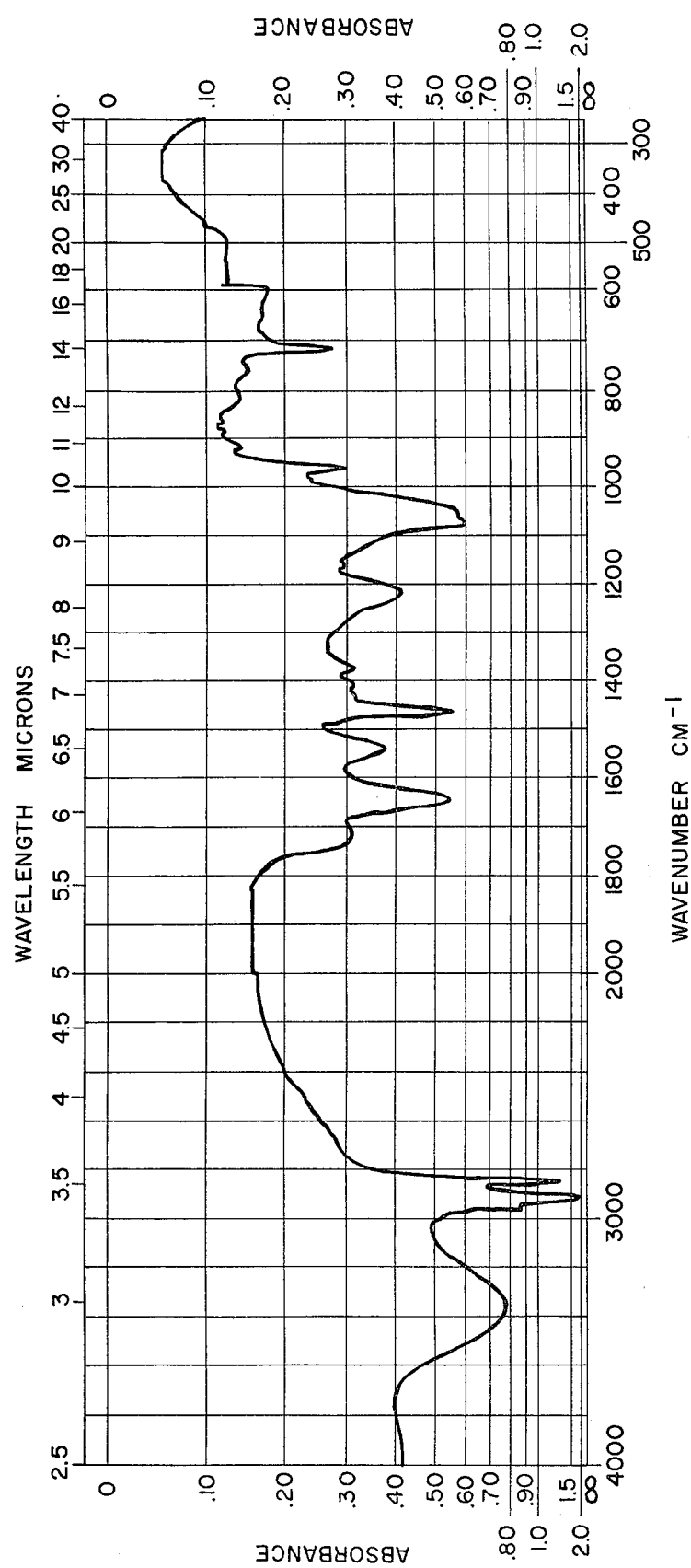

FIG. 1 is an infrared absorption spectrum. It has been mentioned in connection with ionic exchange resins, that these materials select fractions on the basis of their charges. Gel filtration resins employ a completely different principal of separation. They operate on the principal of molecular sieves, that is, they permit the passage of materials through a resin bed on the basis of their molecular weights. In principal it might be said that the gel filtration resins work like sieves in reverse. The larger molecules are excluded by the gel matrix and thus pass immediately through, whereas the smaller particles are withheld by the gel and released in order, according to their decreasing molecular weights. Since the gels are nonionic in nature they are applicable for all materials whether they are cationic, anionic or nonionic.

Gel filtration is a known method for the fractionation of substances in aqueous solutions. It is conducted at any temperature, ambient temperature, and any of the readily available gels being contemplated herein. These gels consist of hydrophilic chains which are cross-linked. They are devoid of ionic groups, the polar character being almost entirely due to high content of hydroxyl groups. While water insoluble, the gels are nevertheless capable of considerable swelling. Macromolecules are completely excluded from the gel phase and migrate through without retention. However, substances of low or intermediate molecular weight penetrate the gel particles to an extent which in most cases is determined by their molecular dimensions and the degree of cross-linkage of the gel. The most frequently employed gel is a dextran gel prepared by cross-linking dextran in such a way that the polysaccharide chains form a macromolecular network of great stability.

Other hydrophylic gels are available, derived for example from starch and polyvinyl alcohol.

Inasmuch as the alcohol extract, usually termed the crude brain extract, serves as the basis for comparison its preparation will now be given.

EXAMPLE A

A crude beef brain extract was prepared from freshly obtained beef brain as follows. After removing the enveloping membrane (pia matter) it was washed free of adhering blood clots and homogenized. It was then mixed with distilled water in the ratio of 1 kilogram brain: 1 liter distilled water and left in the cold room (2°C. to 4°C.) for 20 to 24 hours to form a water extract. At the end of this period, the water extract was filtered through cheese cloth applying light pressure. For complete extraction, the tissues are centrifuged at 2500 rpm for 20 minutes and the extracts combined. This water extract was then deproteinized by adding enough 95 percent ethyl alcohol (3 liters of extract: 16 liters of 95 percent alcohol approximately) to give a final alcoholic concentration of 80 percent. The water-alcohol extract was mixed thoroughly by shaking at periodic intervals over a period of 25 hours at room temperature. It was then vacuum filtered through Whatman No. 1 and the alcohol distilled off under vacuum at 50°C. to 55°C. The alcohol free concentrate was then mixed with Celite, heated to 70°C. to 80°C. and filtered through Celite pads. The filtrate was was stored in the refrigerator and the filtration through Celite pads continued until clear, golden product was obtained. The pH of this extract was adjusted to 7.0, sterilized by Seitz filtration and stored under refrigeration in sterile serum bottles. To test it for antistaphylococcal activity various amounts of crude extract were administered to animals, the amount being determined by ascertaining the dry weights of each batch.

Crude tissue extracts, as mentioned before, consist of a complex mixture of biological materials. As such they are not a completely satisfactory starting material for the type of fractionation procedure contemplated herein. It is desirable, therefore, to use a more pure fraction. Preferably this crude extract is first passed through a bed of particulate adsorbent material such as charcoal or amorphous silicate, the active ingredients being retained thereby. The active ingredients are then eluted therefrom with water at an acid pH and the effluent is percolated through a gel filtration resin.

Charcoal has been used in the past to remove impurities from crude tissue extracts. However, when these materials were tested in vivo it was found that the charcoal filtrate possessed no antimicrobial activity compared to the starting crude. In actuality the fact had been overlooked that the active, more purified fraction was the residue held by charcoal. To illustrate this the following procedure is given for the preparation of the charcoal effluent from crude brain as well as crude spleen, the process again being independent of temperature and pressure.

EXAMPLE B

A volume of the crude tissue extract obtained as in Example A was placed in an Erlenmeyer flask and to it was added 1/10 part of activated Norite A charcoal. The mixture was then stirred well and placed on a mechanical shaker, and oscillated for 15 minutes at 220 oscillations per minute. The suspension was then filtered under vacuum to remove all of the liquid. Next, the charcoal cake was washed with ½ volume of water to insure the elimination of as much of the water-soluble material as possible. The third step involves washing the charcoal with a suitable organic solvent to remove unwanted fatty materials. For this, ethyl alcohol-diethyl ether (1:1) was selected. One volume of the mixture was passed through the cake and filtered under vacuum. When the odor from the organic solvents was no longer noticeable the charcoal was then washed successively with one volume of N/50 HCl and ½ volume of N/10 HCl to obtain the active fraction. In the final step the charcoal was rewashed with one volume of water.

In order to obtain the fraction of this invention from the charcoal effluent gel filtration is employed at this stage. However in the course of assaying fractions for active materials a desirable intermediate step was discovered. Because the pH of some of the fractions was too low for inoculation into the animals, the pH was adjusted to neutrality. It was noted at this time that a brownish flocculent precipitate occurred as the pH neared 7.0. At the acidic pH this fraction is a colorless, clear solution and possesses an odor similar to $H_2S$. As the solution reaches neutrality a yellow flocculent precipitate appears and the odor changes completely. In an attempt to remove all of the insoluble material excess NaOH was added. The insoluble substance was removed by centrifugation, washed with ethanol-ether (9:1) and recentrifuged. The yield of this insoluble substance was very small in comparision to the starting material, approximately 1 percent. A portion of this material was assayed in vivo to determine if it is exhibited any antistaphlococcal activity. The sample, from crude spleen, was inoculated into a group of C3H/HeJ female mice ranging in age from 19 to 21 weeks. In order to solubilize the insoluble precipitate it was placed in N/10 HCl and the animals each received 0.1 milliliter which represented 1.0 milligram of solid material. The inoculations were continued for a three day period, whereas on the fourth day they received a challenge of 0.5 milliliters of a 62 percent suspension of the Original organism. The following results were noted.

Table 1

| Fraction Tested | Number of Animals | Percent Mortality Observed in Hours Post-Challenge | | | | |
|---|---|---|---|---|---|---|
| | | 24 | 48 | 72 | 96 | 120 |
| Untreated (control) | 10 | 50 | 70 | 80 | 80 | 80 |
| Inoculated | 10 | 0 | 0 | 0 | 0 | 0 |

The material was retested to confirm its activity. In this experiment C3H/HeJ male mice ranging in age from 24 to 26 weeks were treated with sample as before. They were challenged with a 60 percent transmission of the Original strain subcutaneously. The results of this experiment are noted in Table 2.

Table 2

| Fraction Tested | Number of Animals | Percent Mortality Observed in Hours Post-Challenge | | | | |
|---|---|---|---|---|---|---|
| | | 24 | 48 | 72 | 92 | 120 |
| Control | 10 | 50 | 70 | 80 | 80 | 80 |
| Inoculated | 10 | 0 | 20 | 20 | 20 | 20 |

From the above results it was concluded that we now had a much more desirable material for the final production of the active principle. It retained the same activity as the crude, and it possessed many of the characteristics thus far investigated.

Throughout the course of these studies, Boontucky and Swiss albino mice, both male and female, were consistantly used except in a very few experiments for comparative purposes. The animals were between 10 and 30 weeks old and had an approximate average weight of 20 to 25 grams. These animals were mostly raised and maintained on the Rockland diet.

All studies, both in vivo and in vitro, were conducted using a penicillin-resistant strain, *Staphylococcus aureus* Original, first isolated from a case of acute tonsilitis and maintained in our laboratories for years. However equivalent results are obtained in the case of bacilli such as *Salmonella typhi*. The *Staphylococcus aureus* strain was preserved in the lyophilized form and stored at 0°C. The lyophilized sample was first cultivated on sterile Difco SA 110 plates and then transferred to slants of the same medium. These slants after 24 hours of growth were stored under refrigeration (approximately 100° C. as the stock cultures). The inoculum was injected subcutaneously in the animals.

The final step in the process is illustrated by the following.

EXAMPLE C

Thirty grams of a dextran gel (Sephadex G-25 obtained from Pharmacia, Uppsala Sweden) were activated by the standard treatment with NaCl and then washed free of chloride. After the column had reached equilibrium a small filter paper disc was placed on the top of the resin bed and the sample was then introduced. The concentration of the sample was always maintained at 10 mg. per milliliter in N/10 HCl and the volume ranged from 15 to 25 milliliters depending on the length of the resin bed. A sample obtained by the processes of Examples A and B was allowed to percolate through the resin and when all had entered it was eluted with distilled water. When the elution had been completed the column was washed with 2 percent HCl to remove any colored material which remained on the column and finally with distilled water and the column was again ready for use.

In the earlier part of the work with the Sephadex resin, consistency in the elution pattern as determined by the pH curve was difficult to maintain. It was found however that once the flow rate had been established this problem no longer existed. It was realized that the slower elution time gave considerably greater resolution of the materials, a fact which is of tremendous importance in isolation studies. Desirably this rate should be one volume of water to 5 to 15 volumes of resin per hour until the elution is complete as determined by the pH.

On elution, the fourth void volume was made up with those fractions whose pH range is between 4 and 5. It was found that this fraction hereinafter named Factor Z was the active fraction. This will be seen from the data.

Assays in vivo of the fraction obtained from the gel filtration show a clear-cut separation of the active material from the rest of the substances present. The results were excellent for several reasons. First, the materials were assayed at a dosage level not in excess of 1 mg. and the protection afforded the animals ranged from 100 percent to 80 percent. These data represented the results obtained from materials repeatedly isolated from both brain and spleen. The animals which survived, in many cases, showed no signs of infection as early as 2 days post-challenge and in certain cases, where lesions had resulted from the infection, there appeared to be complete healing within 5 to 6 days. The extremely active fraction Factor Z of this invention, thus is the aqueous elutant from said gel filtration resin having a pH of 4 to 5 in elution pattern determined by a pH curve. Factor Z is a neutral fraction, insoluble in water, but soluble in acidified water. It is believed to be a mixture of cerebrosides with one of them, phrenosin, predominating. Factor Z is a waxy material having the following characteristics:

Molecular weight: 750–850
After allowance for 5.76% moisture and 1.93% ash the elemental analysis obtained was:

Nitrogen,    1.68%
Carbon,     68.47%
Hydrogen,   11.47%
Oxygen,     18.38% (by difference)

Infrared spectrum: broad band 3400–3300, and other bands at 2910, 2840, 1640, 1540, 1460, 1220, 1070, 960 and 710 CM-1 (mixed with potassium bromide) (FIG. 1).

Factor Z is slightly water soluble, and as will be seen, it possesses outstanding antimicrobial valves, reducing the incidence of deleterious effects of coccic infections. It is contemplated that the factor will be taken orally periodically, as a tablet, say weekly or monthly by those in need of the drug in an amount of 100 to 1000 milligrams doses, preferably 150 to 250 milligram doses. Where contact with staphylococci or streptococci is likely, such as prior to entering a hospital, injections will be used. The factor can be combined with water, vegetable oil, mono-glyceride or di-glyceride vehicle for injection, sodium chloride being used if necessary to render the solution isotonic. In addition, if desired, the water can be removed by distillation at reduced pressure at 40° C., and the material dried to form a solid for use in making tablets. Thus any physiologically acceptable, non-toxic, inert carrier can be used. Suitable colors, lubricants and adhesives can also be added along with solid pharmaceutical carrier to form the tablet or capsule. Suitable carriers are starches, lactose, sucrose and other solid pharmaceutical diluents.

Table 3 represents a composite of a number of prophylactic treatments conducted using various samples of Factor Z obtained by this invention. In these runs all treatments were carried out as previously described and both treatment and challenge were given subcutaneously. The total dosage per animal was in most cases 0.3 mg.; however, in the others it was as low as 0.2 mg. per animal.

Table 3

| Fraction Tested | Percent Suspension Organism | Number of Animals | Percent Mortality Observed in Days Post-Challenge | | | | |
|---|---|---|---|---|---|---|---|
| | | | 1 | 2 | 3 | 4 | 5 |
| Control | 62 | 10 | 60 | 60 | 60 | 70 | 70 |
| Active+ | 62 | 10 | 0 | 0 | 0 | 0 | 0 |
| Control | 60 | 10 | 70 | 90 | 90 | 90 | 90 |
| Active* | 60 | 10 | 0 | 10 | 10 | 10 | 10 |
| Control | 55 | 10 | 60 | 80 | 80 | 80 | 90 |
| Active+" | 55 | 10 | 0 | 0 | 10 | 10 | 10 |
| Active*" | 55 | 10 | 0 | 10 | 10 | 10 | 10 |

*Prepared from crude brain
+Prepared from crude spleen
"Total dosage 0.2 mg.

It is evident from the foregoing that by this invention there is provided an effective process for reducing the incidence of coccic infections in mammals. This is accomplished by providing the mammal, by periodic administration, with the factor described. The preparation of Factor Z according to the practice of the invention will now be exemplified by the following, illustrating all of the steps in a single example.

EXAMPLE D

Crude spleen extract (100 ml. containing 1300 mg.) is stirred with 10 g. of charcoal and filtered, discarding the filtrate. The charcoal is washed with 4 portions (25 ml. each) of a 1:1 mixture of diethyl ether and ethanol. The washings are discarded. The charcoal is then washed with 150 ml. of 0.1 N HCl and filtered, discarding the charcoal. Optionally, to the filtrate there may be added an excess of NaOH solution until precipitation is complete. The suspension is then centrifuged and the supernate discarded. The residue is washed with a 1:1 ether-alcohol mixture and the washings discarded. The residue is dried in a desiccator. The yield at this point is about 70 to 100 mg. or 5 to 7 percent, but the material is active in about 1/40 the concentration of the original crude extract (about a 40-fold concentration of the activity in terms of weight). Further purification of either the filtrate from the charcoal step or the residue from the precipitation is accomplished by adding 250 mg. of this material to 1 N HCl to give a concentration of 25 mg. per ml., and passing this solution through a 12 mm. × 55 cm. column of dextran gel (Sephadex G-25). The column is eluted with water, collecting fractions in a fraction collector. The pH of the fractions is determined and the active material collects in the fractions with a pH range of 4.5 to 4.6. The yield is about 15 mg. from the 250 mg. of partially purified material or from about 3900 mg. of crude extract, an overall yield of about 0.4 percent. This material is active at about 1/10 the dosage of the preceding fraction, equivalent to about a 400-fold overall increase of activity on a weight basis.

In Table 4 are given results when animals were challenged with a 60 percent suspension of *Staphylococcus aureus* after being treated with fractions obtained by Example D.

Table 4

| Source of Fractions | Total dose, mg. | No. Mice | Percent Mortality Observed in Days Post-Challenge | | | | |
|---|---|---|---|---|---|---|---|
| | | | 1 | 2 | 3 | 4 | 5 |
| Control | | 10 | 60 | 60 | 60 | 70 | 70 |
| Spleen | 0.3 | 10 | 0 | 0 | 0 | 0 | 0 |
| Control | | 10 | 70 | 90 | 90 | 90 | 90 |
| Spleen | 0.3 | 10 | 0 | 10 | 10 | 10 | 10 |
| Control | | 10 | 60 | 80 | 80 | 80 | 90 |
| Spleen | 0.2 | 10 | 0 | 0 | 10 | 10 | 10 |
| Brain | 0.2 | 10 | 0 | 10 | 10 | 10 | 10 |

Thus an atimicrobial factor has been isolated from crude tissue extracts which is highly effective in offsetting the lethal effects resulting from staphylococcal infections due to cocci and bacilli. The anitmicrobial factor of this invention, in several hundred animals, is very active at extremely low treatment dosages and demonstrates no toxic in animals. A preliminary experiment in tissues respiration using normal mouse liver demonstrated that no toxic effects occurred as a result of the incubation of the tissue in a medium containing this material when $QO_2$ was measured. Because such a small amount of material was required to give protection to the animals it was felt that our Factor Z is obtained in relatively high purity. Variations and modifications in the processes and uses will obviously occur to those skilled in the art. Thus the extractions and filtrations are ambient temperature and pressure operations. However higher or lower temperatures and pressures can be employed. Such ramifications are deemed to be within the scope of this invention.

What is claimed is:

1. The anticoccic, antibacillic, Factor Z derived from mammalian brain and spleen alcohol extracts by gel filtration having the following characteristics: a slightly water soluble, waxy material having a molecular weight of 750 to 850; an elemental analysis of Nitrogen, 1.68 percent, Carbon 68.47 percent, Hydrogen, 11.47 percent, and Oxygen, 18.38 percent; and the following infrared spectrum as shown in FIG. 1: broad band 3400–3300, and other bands at 2910, 2840, 1640, 1540, 1460 1220, 1070, 960 and 750 $CM^{-1}$ (mixed with potassium bromide).

2. A pharmaceutical composition consisting essentially of an amount of the factor of claim 1 effective against bacillic and coccic infections and a physiologically acceptable, non-toxic, inert carrier.

3. A pharmaceutical composition as claimed in claim 2, in which the amount of the factor present in the carrier is 100 to 1000 mg., per dose.

* * * * *